US012702870B2

(12) United States Patent
Yu

(10) Patent No.: US 12,702,870 B2
(45) Date of Patent: Aug. 11, 2026

(54) MECHANICAL PULSED ULTRASOUND THERAPY FOR MODULATING NEURAL TISSUE MICROENVIRONMENTS

(71) Applicant: Wisconsin Alumni Research Foundation, Madison, WI (US)

(72) Inventor: John-Paul Yu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 84 days.

(21) Appl. No.: 18/200,837

(22) Filed: May 23, 2023

(65) Prior Publication Data

US 2023/0381548 A1 Nov. 30, 2023

Related U.S. Application Data

(60) Provisional application No. 63/346,072, filed on May 26, 2022.

(51) Int. Cl.

*A61N 7/02* (2006.01)
*A61B 90/00* (2016.01)
*A61N 7/00* (2006.01)

(52) U.S. Cl.

CPC .............. *A61N 7/022* (2013.01); *A61B 90/37* (2016.02); *A61B 2090/378* (2016.02); *A61N 2007/0039* (2013.01)

(58) Field of Classification Search

CPC .... A61B 2017/22009; A61B 2090/378; A61B 90/37; A61N 2007/003; A61N 2007/0039; A61N 7/02; A61N 7/022

See application file for complete search history.

(56) References Cited

U.S. PATENT DOCUMENTS

| | | | | |
|---|---|---|---|---|
| 10,183,183 | B2 | 1/2019 | Burdette | |
| 10,772,646 | B2 | 9/2020 | Lu et al. | |
| 10,974,077 | B2 * | 4/2021 | Guha | A61B 5/055 |
| 2007/0083120 | A1 | 4/2007 | Cain et al. | |
| 2010/0069797 | A1 | 3/2010 | Cain et al. | |
| 2011/0028867 | A1 | 2/2011 | Choo et al. | |
| 2012/0004548 | A1 | 1/2012 | Eshel et al. | |

(Continued)

FOREIGN PATENT DOCUMENTS

KR 10-20190094931 8/2019

OTHER PUBLICATIONS

Blackmore, D.G., Turpin, F., Palliyaguru, T. et al. Low-intensity ultrasound restores long-term potentiation and memory n senescent mice through pleiotropic mechanisms including NMDAR signaling. Mol Psychiatry 26, 6975-6991 (2021). https://doi.org/10.1038/s41380-021-01129-7.

(Continued)

*Primary Examiner* — Brooke Lyn Klein
(74) *Attorney, Agent, or Firm* — Boyle Fredrickson, S.C.

(57) ABSTRACT

Short ultrasound pulses or bursts, delivered at intermediate intensity to the target brain tissue transmits acoustic radiation forces into the targeted brain tissue without generating acoustic cavitation and without cellular fractionization. Thus, the present invention exploits the mechanical effects of high-intensity pressure fields only, without cavitation, by optimizing the interaction between acoustic pulses and radiation forces to apply a negative pressure to the brain tissue and degrading the perineuronal nets in the brain tissue and opening the blood-brain barrier.

12 Claims, 8 Drawing Sheets

(56) References Cited

U.S. PATENT DOCUMENTS

| | | | | |
|---|---|---|---|---|
| 2013/0144165 | A1 | 6/2013 | Ebbini | |
| 2014/0094720 | A1* | 4/2014 | Tyler | A61B 5/372 601/2 |
| 2015/0202468 | A1 | 7/2015 | Slayton | |
| 2015/0272601 | A1* | 10/2015 | Dixon | A61N 7/00 604/24 |
| 2016/0038770 | A1* | 2/2016 | Tyler | A61N 7/00 601/2 |
| 2016/0303402 | A1 | 10/2016 | Tyler | |
| 2019/0126317 | A1 | 5/2019 | Pernot | |
| 2020/0147415 | A1* | 5/2020 | Konofagou | A61B 5/389 |
| 2020/0391019 | A1 | 12/2020 | Levy | |
| 2020/0398084 | A1 | 12/2020 | Guha | |
| 2021/0283428 | A1* | 9/2021 | Konofagou | A61N 7/02 |

OTHER PUBLICATIONS

Xia, J., Tsui, PH. & Liu, HL. Low-Pressure Burst-Mode Focused Ultrasound Wave Reconstruction and Mapping for Blood-Brain Barrier Opening: A Preclinical Examination. Sci Rep 6, 27939 (2016). https://doi.org/10.1038/srep27939.

EP Search Report for application No. 23812452.3 dated Apr. 24, 2026. Applicant—Wisconsin Alumni Research Foundation.

* cited by examiner

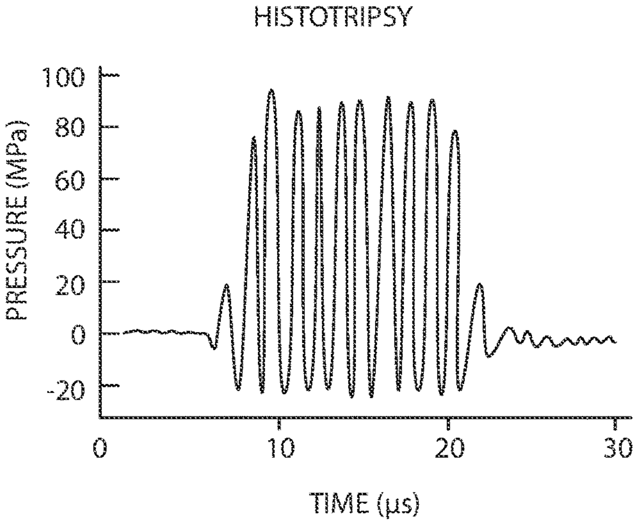

FIG. 1 (Prior Art)

| Parameters | Intrinsic Threshold Histotripsy | Shock-scattering Histotripsy | Boiling Histotripsy | HIFU |
|---|---|---|---|---|
| *Frequency* | 250kHz–3MHz | 500kHz–3MHz | 1–3 MHz | 1–5 MHz |
| *Pulse duration* | 1–2 cycles 0.5–4μs | 3–10 cycles | 100–200 cycles 1–20 ms | Continuous waves or high duty cycle |
| *P-* | >26 MPa | 15–25 MPa | 10–20 MPa | 5–10 MPa |
| *P+* | No requirement | >50MPa | >70MPa | 5–30 MPa |
| *Duty cycle** | ≤1% | ≤1% | ≤2% | 10–100% |
| *PRF* | 1Hz – 1kHz | 1Hz–1kHz | 1Hz–2Hz | – |
| $I_{SPPA}$** | >30 kW/cm$^2$ | 9–40 kW/cm$^2$ | 8–30 kW/cm$^2$ | 0.5–10 kW/cm$^2$ |
| $I_{SPTA}$*** | 0.5–300 W/cm$^2$ | 1–400 W/cm$^2$ | 50–600 W/cm$^2$ | 100–5000 W/cm$^2$ |
| *Number of pulses* | 50–2000 | 50–2000 | 1–100 | – |
| *Bioeffect* | Mechanical tissue liquefaction | | Mechanical tissue liquefaction | Thermal necrosis |
| *Mechanism* | Inertial cavitation | | Boiling cavitation | Thermal |

*Duty cycle: ultrasound on-time/total treatment time; **$I_{SPPA}$: Spatial peak pulse average intensity;

***$I_{SPTA}$:Spatial peak time average intensity.

FIG. 2 (Prior Art)

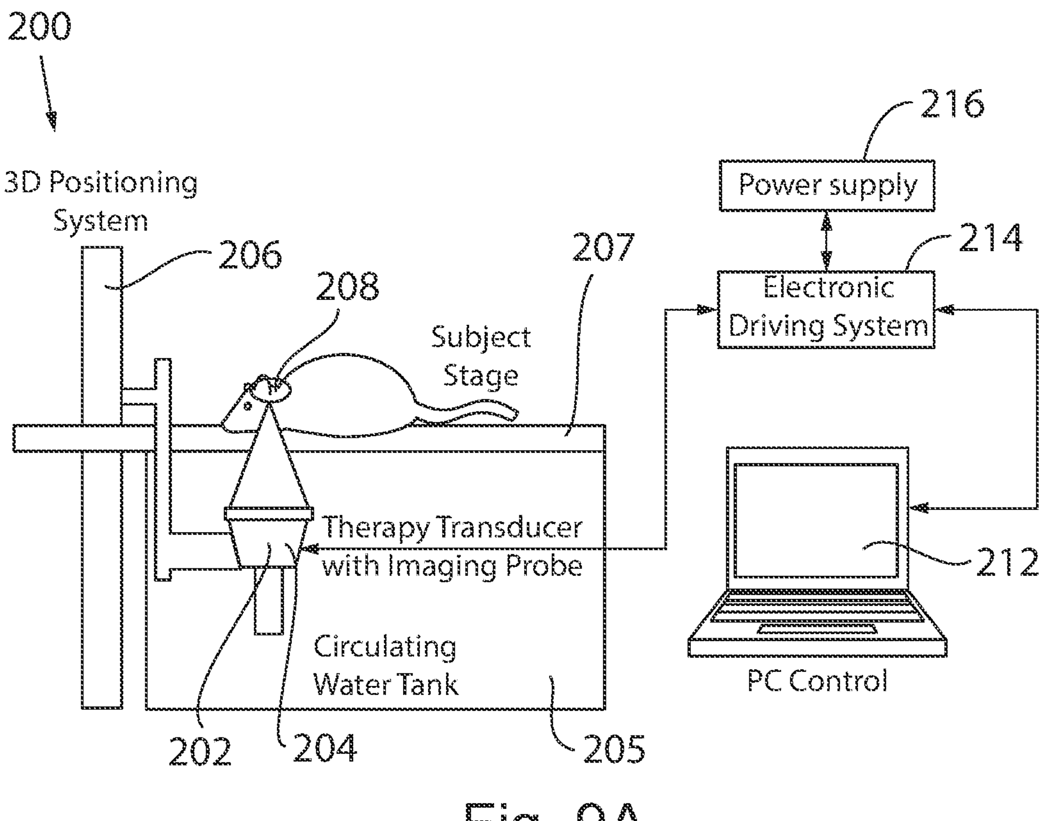
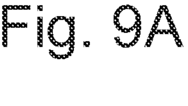
Fig. 9A
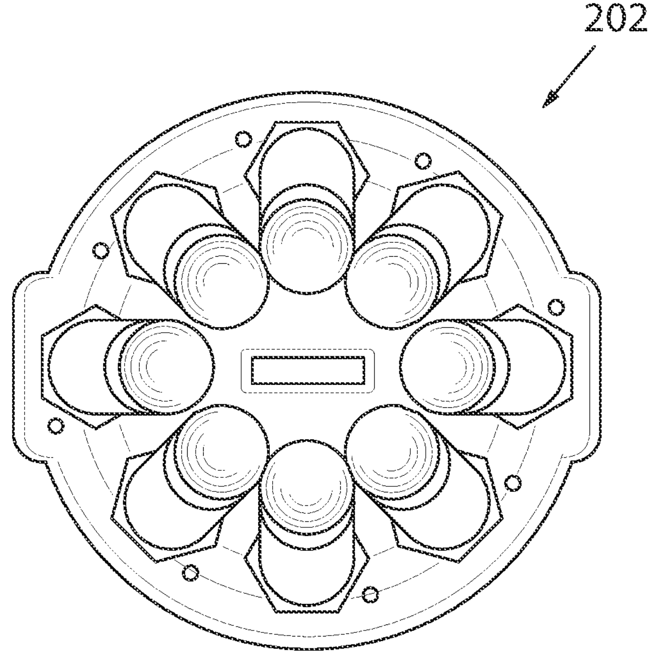
Fig. 9B

| Experimental Parameters | | | | |
|---|---|---|---|---|
| | Experimental Group | Peak Negative Pressure (MPa) | Duty Cycle (%) | Exposure Duration (sec) |
| Low[a] | 1 | 1 | 10 | 10 |
| Low | 2 | 1 | 10 | 30 |
| Low | 3 | 1 | 10 | 60 |
| Intermediate | 4 | 10 | 2 | 10 |
| Intermediate | 5 | 10 | 2 | 30 |
| Intermediate | 6 | 10 | 2 | 60 |
| High | 7 | 20 | <1% | 10 |
| High | 8 | 20 | <1% | 30 |
| High | 9 | 20 | <1% | 60 |

| Experimental Parameters | | | | |
|---|---|---|---|---|
| | Experimental Group | Peak Negative Pressure (MPa) | Duty Cycle (%) | Exposure Duration (sec) |
| Low[a] | 1 | 1 | 10 | 10 |
| Intermediate | 2 | 10 | 2 | 30 |
| High | 3 | 20 | <1% | 30 |
| High | 4 | 20 | <1% | 60 |

MECHANICAL PULSED ULTRASOUND THERAPY FOR MODULATING NEURAL TISSUE MICROENVIRONMENTS

CROSS-REFERENCE TO RELATED APPLICATIONS

This application claims the benefit of U.S. Provisional Patent Application No. 63/346,072, filed May 26, 2022, which is incorporated by reference herein in its entirety.

BACKGROUND OF THE INVENTION

The present invention relates to focused ultrasound (FUS) techniques focused on target volumes inside the body in a manner which induces tissue disturbance and more particularly to focused ultrasound techniques that alter neural tissue microenvironments without ablation, cavitation, or heating effects.

The development of high-intensity focused ultrasound (HIFU) to noninvasively treat disease is part of a comprehensive drive towards less invasive yet effective treatments. With focused ultrasound, an acoustic lens is used to concentrate multiple intersecting beams of ultrasound on a target deep in the body with extreme precision and accuracy.

Histotripsy is a focused ultrasound technique which applies acoustic energy generated by an extracorporeal ultrasound transducer focused on a target volume within the body. Histotripsy exploits the mechanical effects of high-intensity pressure fields to impart mechanical stresses and strains on the cells and tissues of the target volume producing cellular and tissue disruption, i.e., tissue ablation, but with a very low duty cycle to minimize tissue heating.

Specifically, histotripsy optimizes the interaction between acoustic pulses and gas filled microbubbles, i.e., cavitation nuclei, within the human tissue. The process employs high intensity sound waves and short ultrasound (US) pulses or bursts to initiate acoustic cavitation. Acoustic cavitation occurs when a sufficiently negative pressure is applied to the tissue, and specifically, is applied to the endogenous gas present in the tissue to cause microbubble formation from fluid vaporization and release of dissolved gas. Once formed, the microbubbles exhibit highly dynamic patterns of oscillation and inertial collapse. The mechanical action of rapid expansion and collapse of dense clouds of microbubbles or "cavitation clouds" impart severe strains and stresses repeated over many US pulses to disrupt the cells and tissues immediately surrounding the cavitation bubbles. The cavitation clouds are thus controllable to accurately destroy the cells and tissues in the target volume, rendering the tissue into acellular debris. The acellular debris of the target region is then absorbed into the body, for example, within 1 to 2 months, and ablating the tissue. The duty cycle of the US pulses is kept very low (e.g., ≤4% and sometimes ≤2% and sometimes ≤1%) to minimize tissue heating, thus, giving the tissue time to cool between pulses preventing thermal damage.

Referring to the US pulse seen in FIG. 1, typical histotripsy parameters employ extremely high pressure waves with high pressure amplitudes (e.g., peak positive pressure (P+) of at least 50 MPa and peak negative pressure (P−) of at least 15 MPa) to the tissue to generate acoustic cavitation which occurs when the negative pressure threshold is reached within the tissue (e.g., less than 28 MPa for most tissues). Thus, the "cavitation threshold" is the minimum negative pressure amplitude at which pre-existing microbubbles in the tissue begin to oscillate or collapse.

Typical histotripsy parameters (e.g., for intrinsic threshold, shock-scattering, boiling type histotripsy procedures) used to reach the cavitation threshold compared to HIFU parameters are summarized in the table of FIG. 2.

Histotripsy provides several advantages to conventional thermal ablation methods such as HIFU because it is non-thermal, non-invasive, and provides high precision, real-time monitoring/feedback and tissue liquefaction. For example, using histotripsy, tissue ablation can be confined to highly precise target volumes guided by real-time ultrasound monitoring of treatment progression. The histotripsy process can be used to isolate cavitation mechanical effects and minimize tissue heating effects. The result is fractionated tissue that appears hypoechoic as many of the structures that would have reflected ultrasound energy have been broken down and homogenized.

Current clinical applications for histotripsy include treatments and therapies for breast cancer, prostate cancer, several cardiac applications, and various benign diseases including prostatic benign prostatic hyperplasia (BPH) and breast fibroadenoma.

Methods of using pulsed cavitational ultrasound therapy are described in U.S. 2007/0083120 and U.S. 2010/0069797, both entitled, "Pulsed cavitational ultrasound therapy," and hereby incorporated by reference.

SUMMARY OF THE INVENTION

The present inventor has found that employing short ultrasound pulses or bursts, but at a lower, intermediate intensity to the target tissue (compared to high-intensity pulses delivered during histotripsy) will cause acoustic radiation forces to be transmitted into the target tissue without generating acoustic cavitation and without cellular fractionization. Thus, the present invention exploits the mechanical effects of high-intensity pressure fields without cavitation and without heating by optimizing the interaction between acoustic pulses and radiation forces to apply a negative pressure to the tissue but that does not reach the negative pressure threshold necessary to cause cavitation encountered in histotripsy.

Thus, the acoustic pulses of the present invention provide smaller pressure waves (i.e., lower peak positive and negative pressure amplitudes) while still producing precise and accurate lesions of disturbed tissue with sharp boundaries between treated and untreated tissue.

Further, the narrow width of each ultrasound pulse highly restricts the degree to which bone aberrations, such as from ribs or skull, can induce and distort the ultrasound focus and the short pulse duration allows the ultrasound pulses to be delivered rapidly while maintaining low duty cycles to avoid complications of tissue heating that are often encountered in other FUS technologies such as HIFU.

The present invention provides pulsed ultrasound therapy for mechanical tissue shaping (i.e., the "histoplasty" process) coupled with real-time monitoring/feedback which provides tissue disturbance (i.e., shear forces, compressive forces, high pressure, chemical effects, conformational effects) without cavitation and cellular fractionization while minimizing known limitations such as tissue heating, ultrasound aberration, and tissue inflammation that are associated with other microbubble-based focused US approaches such as histotripsy.

The mechanical effects of the tissue disturbance without cellular fractionization can achieve a wide range of non-ablative soft tissue bioeffects depending on the targeted tissue and the peak pressure amplitudes use.

The present invention contemplates a new non-thermal, non-cavitary therapeutic regime of focused ultrasound whereby high amplitude ultrasound pulses generate biologically salient mechanical forces in target tissues to achieve a broad range of desired tissue bioeffects.

In one embodiment of the present invention, the present invention provides a targeting of perineuronal nets (PNNs) as a salient therapeutic target for FUS. A non-thermal, non-cavitary therapeutic regime of FUS therefore produces biologically salient mechanical forces in the brain to achieve desired tissue bioeffects such as the modulation of PNN density.

In an alternative embodiment of the present invention, the present invention provides a targeting of blood-brain barrier (BBB) disruption to advance the targeted delivery of biotherapeutics to the central nervous system (CNS). A non-thermal, non-cavitary therapeutic regime of FUS therefore produces biologically salient mechanical forces in the brain to achieve desired tissue bioeffects such as the opening of the BBB and permitting the transit of therapeutics from the intravascular compartment to the brain.

There exist numerous potential applications of a FUS technique expressly designed to alter the extracellular matrix (ECM) of the CNS and the BBB. Within the CNS, these include the application of histoplasty to study traumatic brain injury and the effect of blunt trauma on the ECM of the brain and the potential use of histoplasty to reduce tissue fibrosis and tissue stiffening around chronic indwelling neural implants. Beyond the CNS, a FUS method explicitly designed to target ECM with non-ablative mechanical bioeffects can be applied to alter the tumor microenvironment in neoplasia and metaplasia or for the potential treatment of musculoskeletal conditions like calcific tendonitis. These cross-cutting applications across organ systems and disease categories highlight the substantial potential impact of the histoplasty technique and the innovative therapeutic applications that histoplasty can spur.

The present invention provides a method for controlled mechanical degradation of an extracellular matrix of brain tissue having a cavitation threshold initiating a bubble cloud in the brain tissue, comprising outputting a treatment ultrasound pulse sequence at a treatment portion of the extracellular matrix of the brain without initiation of a bubble cloud in said treatment portion of the extracellular matrix of the brain in response to the treatment ultrasound pulse sequence; wherein the treatment ultrasound pulse sequence is at a pulse intensity that is less than the cavitation threshold and at least partially degrades perineuronal nets of the brain tissue in the treatment portion and without initiating a bubble cloud in the brain tissue.

It is thus a feature of at least one embodiment of the invention to provide mechanical tissue effects without tissue ablation and without tissue heating.

A peak negative pressure of the treatment ultrasound pulse sequence may be less than or equal to 20 MPa. A peak negative pressure of the treatment ultrasound pulse sequence may be less than or equal to 15 MPa. A peak negative pressure of the treatment ultrasound pulse sequence may be less than or equal to 10 MPa.

A peak positive pressure of the treatment ultrasound pulse sequence may be less than MPa.

A frequency of the treatment ultrasound pulse sequence may be between 500 kHz and 1 MHz.

A pulse repetition frequency (PRF) of the treatment ultrasound pulse sequence may be between 250 Hz and 750 Hz.

A duty cycle of the treatment ultrasound pulse sequence may be less than or equal to 10%. A duty cycle of the treatment ultrasound pulse sequence may be less than or equal to 2%. A duty cycle of the treatment ultrasound pulse sequence may be less than or equal to 1%.

The pulse length of the treatment pulse may be less than or equal to 15 psec. A pulse length of the treatment pulse may be less than or equal to 20 psec.

A number of pulses in the treatment ultrasound pulse sequence is 10 to 50 pulses.

An exposure duration of the treatment ultrasound pulse sequence is less than 60 sec.

The method may further comprise the step of monitoring an amount of degradation of the extracellular matrix of the brain tissue in the treatment portion.

The method may further comprise the step of adjusting the treatment ultrasound pulse sequence based on the amount of degradation of the extracellular matrix of the brain tissue in the treatment portion.

An alternative embodiment of the present invention provides a method for controlled mechanical deformation of blood-brain barrier (BBB) tissue having a cavitation threshold initiating a bubble cloud in the brain tissue, comprising outputting a treatment ultrasound pulse sequence at a treatment portion of the extracellular matrix of the brain without initiation of a bubble cloud in said treatment portion of the extracellular matrix of the brain in response to the treatment ultrasound pulse sequence; wherein the treatment ultrasound pulse sequence is at a pulse intensity that is less than the cavitation threshold and at least partially deforms the blood-brain barrier tissue in the treatment portion without initiating a bubble cloud in the brain tissue.

The method may further comprise the step of monitoring an amount of opening of the BBB.

The method may further comprise the step of adjusting the treatment ultrasound pulse sequence based on the amount of opening of the BBB.

These particular objects and advantages may apply to only some embodiments falling within the claims and thus do not define the scope of the invention.

BRIEF DESCRIPTION OF THE DRAWINGS

FIG. 1 is an exemplary graph showing prior art waveforms of the ultrasound pulses delivered during histotripsy treatments;

FIG. 2 is a table showing typical histotripsy parameters (e.g., for intrinsic threshold, shock-scattering, boiling type histotripsy procedures) used to reach the cavitation threshold compared to HIFU parameters;

FIG. 9 is a schematic of an exemplary small animal histotripsy system showing (A) a complete experimental FUS system and (B) an 8-element, 1 MHz custom transducer built using rapid prototyping fabrication methods;

DETAILED DESCRIPTION OF THE INVENTION

Ultrasound waves interact with soft tissue in numerous ways to yield a range of biophysical effects. Broadly, these bioeffects can be divided into "thermal" and "non-thermal" mechanisms.

"Thermal" bioeffects of FUS have been extensively studied and are harnessed to perform targeted non-invasive thermal ablations throughout the body. For example, in the central nervous system, magnetic resonance-guided FUS has been approved by the U.S. Food and Drug Administration to ablate a single focal volume in the central nervous system as a therapy for essential tremor.

"Non-thermal" bioeffects are mechanical bioeffects present during insonation with FUS. Although the mechanical bioeffects associated with FUS are generally considered ancillary and representative of how ultrasound energy is dissipated in tissue, recent work demonstrates the capacity for FUS to generate clinically salient non-thermal mechanical bioeffects for therapeutic applications without the use of heat. Histotripsy uses pressure waves with high rarefactional (negative) amplitudes to draw dissolved gas out of liquid tissue to form cavitation bubbles, which then undergo inertial cavitation to cause targeted non-thermal and mechanical ablation of tissue. However, beyond tissue ablation, the present invention contemplates that FUS can be used to produce other mechanical bioeffects in soft tissues.

Figure 3:
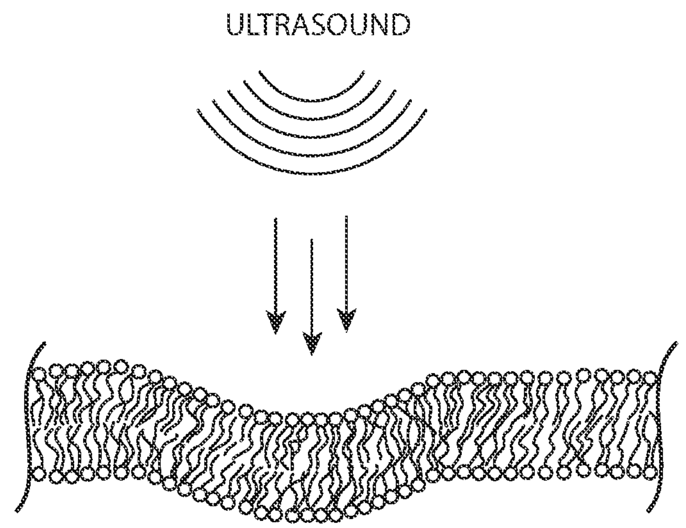
FIG. 3 is a schematic diagram of a mechanical interaction between ultrasound waves and soft tissue and cells of the patient tissue to exhibit deformation of the tissue through shear stress waves in accordance with the teachings of the present invention.

Referring to FIG. 3, the present invention contemplates the use of intermediate-intensity ultrasound directed to the target tissue (i.e., without tissue ablation or bulk tissue fractionization which fractionates portions of a cell or fractionates on a cellular level) to produce mechanical bioeffects in soft tissue such as would cause mechanical deformation, mechanical disruption of the tissue, or cellular or tissue remodeling to change tissue or cellular interactions to produce desired effects without cavitation.

Therefore, the present invention produces mechanical bioeffects without heating and without bubble formation using intermediate amplitude acoustic therapy pulses.

Focused Ultrasound for Mechanical Tissue Shaping

The present disclosure uses pulsed non-thermal, non-cavitational high intensity focused ultrasound to affect tissue shaping assisted processes such as mechanical deformation, cell or tissue remodeling, and drug delivery, in a predictable and controllable manner for mechanically affecting tissues for therapeutic applications. The pulsed non-thermal, non-cavitational therapy process is similar to histotripsy, in that soft tissues are mechanically disturbed, but does not employ cavitation to induce cellular destruction. The present process of pulsed non-thermal, non-cavitational ultrasound is also referred to herein as histoplasty, connoting essentially the "shaping" of soft tissues. The histoplasty process of the present teachings can, at least in part, involve the mechanical movement of tissue, i.e., stresses and strains, without the creation and maintenance of ensembles of microbubbles and, in some embodiments, the use of feedback in order to optimize the process based on observed stress and strain tissue dynamics in real time.

In the past, cavitation was avoided in therapeutic applications because its results were unpredictable with regards to both location of damage and thresholds for damage production, and therefore, the damage produced was spatially irregular. However, through the invention of the histotripsy process, pulsed ultrasound was used to produce microbubbles, both in the form of contrast agents and/or other active agents infused into the body or bubbles formed from previous ultrasound exposure, to allow for more predictable damage location and thresholds, with much lower incident intensities for damage production, and production of much more spatially regular lesions.

The present invention builds on this existing technology by using pulsed ultrasound in a manner which uses predictable cavitation thresholds to avoid the production of microbubbles but still providing much lower incident intensities for damage production and production of much more spatially regular lesions. In this respect, the problems and limitations of existing US techniques such as HIFU and histotripsy of tissue heating, ultrasound aberration, and tissue inflammation have been improved to produce tissue remodeling instead of tissue destruction or ablation.

Figure 4:
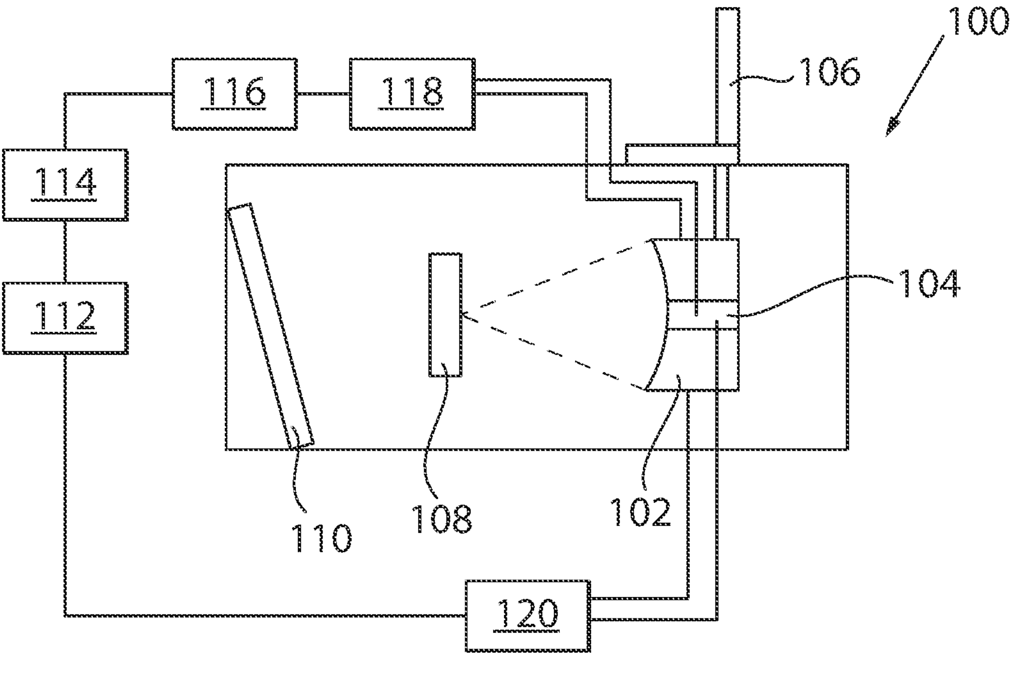
FIG. 4 is a schematic illustration of an exemplary apparatus for performing pulsed non-thermal, non-cavitational ultrasound therapy constructed in accordance with the teachings of the present invention.

Referring to FIG. 4, an exemplary apparatus 100 for performing pulsed non-thermal, non-cavitational ultrasound therapy constructed in accordance with the teachings of the present disclosure is shown. The apparatus can comprise a therapy transducer 102 and a monitoring transducer 104 coupled to a 3-axis positioning system 106. The therapy transducer 102 and monitoring transducer 104 focus ultrasound onto the target tissue 108, backed by a sound absorber 110. Computer control and data collection 112 is coupled to a function generator 114 that is coupled to an amplifier 116 that is coupled to a matching circuit 118 that is coupled to the transducers 102, 104. Computer control and data collection 112 are also coupled to a digital oscilloscope 120, which is further coupled to the transducers 102, 104.

Pulsed non-thermal, non-cavitational ultrasound therapy, or the histoplasty process, according to the present teachings, may include the following steps, namely: therapy step (histoplasty) and feedback step, which are described in further detail below.

During the therapy step, the target volume which is mostly void of micro-nuclei (i.e., small microbubbles) is impinged upon by therapy pulses that produce acute tissue deformation. Each therapy pulse can produce just a small part of the overall therapy effect, which can include mechanical tissue deformation. The overall therapy effect may include applying shear stress and strain on the tissue, applying positive and negative pressure on the tissue, inducing chemical changes in the tissue based on the mechanical deformation, and the like associated with the mechanical forces applied to the tissue.

In one embodiment, the therapy produces the desired therapy effect during the therapy step. In one embodiment, in the therapy step, a series of intermediate intensity pulses are focused into the therapy volume sufficient to produce mechanical deformation but is below a value that would initiate bubble clouds. This intermediate intensity is sufficient to produce adequate mechanical deformation without cavitation. As will be described herein, feedback on the mechanical deformation can be obtained by monitoring the therapy pulse backscatter from the tissue. The backscatter is monitored by the therapy transducer (or subset of therapy transducer array elements) in the receive mode, or by a simple (and separate) monitoring transducer. In some embodiments, multiple transducers can be employed for monitoring feedback.

During the feedback step, the treatment step can be monitored to thereby check overall therapy progression. The feedback and monitoring step allows for various parameters of the pulsed non-thermal, non-cavitational ultrasound process to be varied in real time or in stages, if desired, permitting controlled administration of the ultrasound therapy. For example, the process can be terminated, the extent of therapy measured, and the process restarted. In particular, the feedback step enables adjustment and tuning of the histoplasty process in precise and controlled ways previously unobtainable.

It should be noted that methods of the present teachings can include variations where each of these steps can use different methods of energy delivery with different forms of energy and different feedback schemes. Additional details of various embodiments of each step follow.

Figure 5:
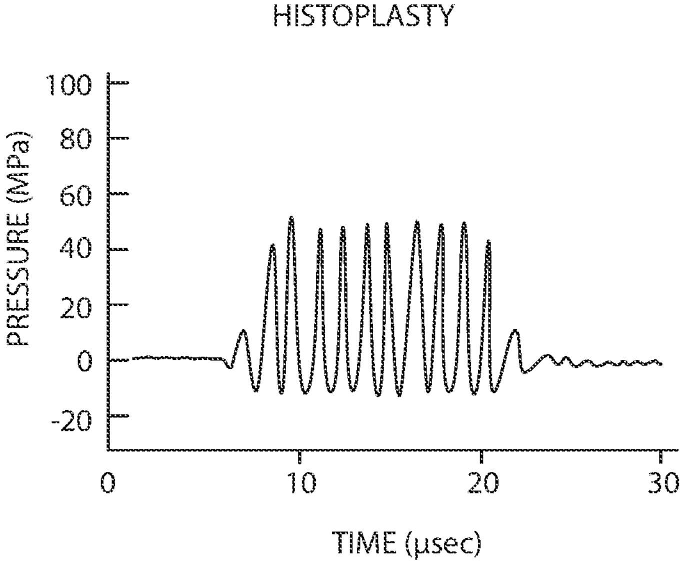
FIG. 5 is an exemplary graph showing waveforms of the ultrasound pulses delivered using the apparatus of FIG. 4 during histoplasty treatments according to the teachings of the present invention.

Therapy Step:

Referring also to FIG. 5, therapy can comprise of a therapy pulse sequence, which is also referred to herein as a therapy sequence, therapy pulse, or therapy. The therapy process is the interaction of ultrasound on therapy tissue to produce tissue deformation (without cavitation and without mechanically subdividing the tissue) within the therapy volume. Therapy energy in the histoplasty process can be acoustic (e.g., ultrasonic).

The transducer or transducers can be either single focus, or multi-focus, or phased arrays where the focus can be scanned in 1, 2, or 3-dimensions. The therapy transducer(s) can be contiguous spatially or can be separated spatially, using multiple windows into the therapy volume. The transducers can also operate at different frequencies individually or as an overall ensemble of therapy transducers. The therapy transducer(s) can also be mechanically scanned to generate larger therapy zones and/or a combination of mechanically and electronically (phased array) scans can be used. The therapy transducer(s) can be intimately involved in the feedback processes and procedures as sources of interrogation sequences or as receivers (or even imagers).

The multiplicity of transducers enables various embodiments where one of the therapy transducers could operate at a significantly lower frequency from the other(s).

In some embodiments, one or more low frequency transducers can act as a “pump” with the other transducer(s) sending pulses (i.e., for therapy or feedback) propagating along with the low frequency pump. For example, if a higher frequency, short therapy pulse arrives in the therapy volume in a particular relation to the phase of the low frequency pump pulse, multiple effects can be obtained therefrom depending on this relative phase relationship. In one embodiment, if the higher frequency pulse arrives at the therapy volume on the peak positive pressure of the pump, the cavitational effect is reduced. Also, if the pump and therapy pulse arrive at different propagation angles, it can serve to spatially sharpen the effective focus of the therapy pulse. The maximum sharpening effect occurs when the pulses arrive having been propagated in opposite directions or 90 degrees from each other.

The therapy transducers (i.e., high and low frequencies) can also operate in conjunction with the feedback transducers to enhance effects. For example, if an imaging transducer is used for feedback, it can be used to enhance the detection of unwanted microbubbles or nuclei. That is, if the imaging pulse arrives in the imaging volume on the rarefactional trough of the pump pulse, any nuclei or microbubbles will have expanded and will be relatively hyperechoic. If the imaging pulse arrives on the peak positive pressure, the nuclei or microbubbles will be smaller in size (compressed) and the image in this interaction zone will be relatively hypoechoic. Thus, by using a difference image, one will see only microbubble activity as the other tissue echoes will be constant (same) in both images.

In some embodiments, the therapy pulse can be used as a pump and the imaging pulse can be propagated therewith. If one or more therapy pulses are focused on a therapy volume or portion of a therapy volume, the intensity can be greater in the focused therapy volume. Therefore, the mechanical effect on tissue will be greater in the focused therapy volume and less away from the focused therapy volume. By co-propagating the imaging and therapy pulse alternately, with the imaging pulse riding on the peak rarefactional pressure of the therapy pulse and the peak positive pressure of the therapy pulse, a difference image will show the greatest difference near the focused therapy pulse(s). The difference will be less away from the focused therapy pulse(s). Thus, this scheme allows direct imaging of the therapy pulse beam pattern. This can be used to identify and locate where the maximum mechanical deformation will occur in the therapy volume before treatment.

Feedback & Monitoring Step:

In some embodiments, feedback enables assessment of parameters related to noninvasive image guided therapy or drug delivery. The methods and devices depend on the fact that the actual therapeutic effect is the progressive mechanical deformation of the tissue that can also provide enhanced drug transport (or other therapeutic or diagnostic effect) over one or more therapy pulses. Thus, the tissues exposed to the histoplasty process are changed physically. These physical changes are much more profound than changes produced by competing therapies. Furthermore, embodiments of the present teachings make it possible to monitor the therapeutic effectiveness both during and after the therapy process.

In some embodiments, feedback and monitoring can include monitoring changes in: speckle reduction in backscatter; backscatter speckle statistics; mechanical properties of tissue (i.e., elastography); shear wave propagation; acoustic emissions, and electrical impedance tomography, as described in more detail below.

Backscatter, Speckle Reduction: Progressively mechanically deformed tissue, in other words disrupted or moved tissue, results in changes in the distribution of acoustic scatter. At some point in the process, the tissue is disrupted or changed in position enough where little ultrasound is scattered, or the amount scattered is reduced significantly. This results in a significant reduction in speckle, which is the coherent constructive and destructive interference patterns of light and dark spots seen on images when coherent sources of illumination are used; in this case, ultrasound. After some treatment time, the speckle reduction may result in a dark area in the therapy volume. Since the amount of speckle reduction is related to the amount of tissue disruption, it can be related to a change in orientation of the tissue and cells. So, treatment can proceed until a desired speckle reduction level has been reached. Speckle is easily seen and evaluated on standard ultrasound imaging systems. Specialized transducers and systems can also be used to evaluate the backscatter changes.

Backscatter, Changes in Speckle Statistics: Speckle in an image persists from frame to frame and changes little as long as the scatter distribution does not change and there is no movement of the imaged object. However, long before the scatters are reduced enough in size to cause speckle reduction, they may be changed sufficiently to be detected by signal processing and other means. This family of techniques can operate as detectors of speckle statistics changes. For example, the size and position of one or more speckles in an image will begin to decorrelate before observable speckle reduction occurs. Speckle decorrelation, after appropriate motion compensation, can be a sensitive measure of the mechanical disruption of the tissues, and thus a measure of therapeutic efficacy. This feedback and monitoring technique permits early observation of changes resulting from the histoplasty process and can identify changes in tissue. For example, this method can be used to monitor the histoplasty process for enhanced drug delivery where tissue is spatially disrupted.

Elastography: As the tissue is further deformed or disrupted, its mechanical properties change from a soft but interconnected solid to a disconnected solid with less cellular interactions. These changes in mechanical properties can be measured by various imaging modalities including MRI and ultrasound imaging systems. For example, an ultrasound pulse can be used to produce a force (i.e., a radiation force) on a localized volume of tissue. The tissue response (displacements, strains, and velocities) can change significantly during histoplasty treatment allowing the state of tissue disruption to be determined by imaging or other quantitative means.

Shear Wave Propagation Changes: The disruption of tissues makes the tissue more "fluid" and less solid and fluid systems generally do not propagate shear waves. Thus, the extent of tissue fluidization (or when cells are connected to less neighboring cells or there are less cellular interactions) provides opportunities for feedback and monitoring of the histoplasty process. For example, ultrasound and MM imaging systems can be used to observe the propagation of shear waves. The extinction of such waves in a treated volume is used as a measure of tissue distortion or disruption. Moreover, dedicated instrumentation can be used to generate and measure the interacting shear waves. For example, two adjacent ultrasound foci might perturb tissue by pushing it in certain ways. If adjacent foci are fluidized, no shear waves propagate to interact with each other. If the tissue is not fluidized, the interaction would be detected with external means, for example, by a difference frequency only detected when two shear waves interact nonlinearly, with their disappearance correlated to tissue disruption.

Acoustic Emission: As a tissue volume is disturbed, its effect on microbubbles formation in the tissue is changed. For example, microbubbles may grow more easily and have a different lifetime and collapse changing characteristics in intact versus disturbed tissue. Microbubbles may also move and interact after mechanical deformation producing larger bubbles or cooperative interaction among bubbles, all of which can result in changes in acoustic emission. These emissions can be heard during treatment and they can change during treatment. Analysis of these changes, and their correlation to therapeutic efficacy, enables monitoring of the progress of therapy.

Electrical Impedance Tomography: An impedance map of a therapy site can be produced based upon the spatial electrical characteristics throughout the therapy site. Imaging of the conductivity or permittivity of the therapy site of a patient can be inferred from taking skin surface electrical measurements. Conducting electrodes are attached to a patient's skin and small alternating currents are applied to some or all of the electrodes. One or more known currents are injected into the surface and the voltage is measured at a number of points using the electrodes. The process can be repeated for different configurations of applied current. The resolution of the resultant image can be adjusted by changing the number of electrodes employed. A measure of the electrical properties of the therapy site within the skin surface can be obtained from the impedance map, and changes in tissue in the histoplasty process can be monitored using this process.

Second-Harmonic Imaging Microscopy: The cell and tissue structure and function can be visualized using a microscope imaging contrast mechanism such as second-harmonic imaging microscopy (SHIM) which obtains contrasts from variations in a tissue specimen's ability to generate second-harmonic light from incident light. An intense laser light passes through the tissue (having a non-centrosymmetric molecular structure) which is either inherent or induced externally, for example, by an electric field. By using near infrared wavelengths for the incident light, SHIM can construct three-dimensional images of specimens by imaging deeper into thick tissues. A comparison of images can give insight about the changes in the microstructure of the tissue or collagen structure that can be monitored using this process, for example, as described in Example 2 below.

Histoplasty Parameter Adjustments:

In some embodiments of the present teachings, opportunities exist to adjust or customize the histoplasty process for particular applications. By changing various parameters, intermediate-intensity pulses can be delivered, therapy intensity varied, and changes in treatment pulses can be realized. The aforementioned feedback and monitoring methods readily allow these directed parameter adjustments and the effects thereof to be observed during the histoplasty process, in real time, and/or permit therapy progress measurement in stages, where therapy can be reinitiated as desired or as necessary.

Intensity thresholds of treatment pulses can also be varied as needed. The feedback and monitoring methods of the present disclosure allow changes in intensity to be observed in real time or in stages as desired. Changes in intensity can identify and tune intensity thresholds for ultrasound induced mechanical deformation in order to achieve localized and discrete soft tissue disruption without cavitation.

Additional parameter adjustments can affect the structure of tissue lesions produced by the histoplasty process. For example, adjustment of specific acoustic parameters, such as pulse sequence repetition frequency (PRF) and sustaining pulse amplitude, can result in marked effects on the physical characteristics of resulting tissue damage. Sensitivity of disrupted tissue production to acoustic input parameters can provide a means by which to exert control over the degree to which the mechanical effects of localized ultrasound are responsible for lesion formation.

Therapeutic Applications:

In some embodiments, the pulsed non-cavitational ultrasound methods of the present teachings permit various therapeutic procedures, including tissue deformation via controlled mechanical movement of soft tissue, cell or tissue remodeling, or drug delivery and activation, to be accomplished either wholly from means external to the body, or with minimal dependence on procedures no more invasive than current endoscopic techniques. Being noninvasive, the cost advantages, both in hospital stay and in surgical preparation time, are readily apparent. In addition, the reduction or absence of cosmetic disfigurement and risk of infection are both significant advantages. While this noninvasive property is shared with other ultrasound based delivery methods, histoplasty according to the present teachings has several potential advantages over current approaches.

In some embodiments, therapies based on the present teachings can include the following features: ability to use a low ultrasound frequency, which will not heat intervening tissue; ability to use a frequency low enough to propagate through some bone interfaces such a ribs or skull; and ability to use a frequency low enough to make phased array element sizes larger thus significantly reducing array and driving system costs.

In some embodiments, therapies based on the present teachings can include the following features: ability to use a very short pulse duration (e.g., a few microseconds in length) to exert increased oscillatory forces and shear stress on the tissue; ability to use a very short pulse duration to increase the wave momentum applied to the target tissue; and ability to use a very short pulse duration (along with the high pulse repetition frequency) to maintain low constant duty cycle (e.g., ≤1% or ≤2%) and minimize heating effects on the tissue.

In some embodiments, therapies based on the present teachings can include the following features: ability to use a high pulse repetition frequency (PRF) to exert increased pressure on the target tissue; and ability to use a high pulse repetition frequency (PRF) (along with the short pulse duration) to maintain low constant duty cycle (e.g., ≤1% or ≤2%) and minimize heating effects on the tissue.

In some embodiments, therapies based on the present teachings can include the following features: ability to use a low constant duty cycle (e.g., ≤1% or ≤2%) to minimize heating effects (thermal damage) on the target tissue; ability to use a low constant duty cycle (e.g., ≤1% or ≤2%), which will not heat intervening tissue; and ability to use a low constant duty cycle (e.g., ≤1% or ≤2%) to minimize thermal damage to adjacent tissue structures by heat diffusion.

In some embodiments, therapies based on the present teachings can include the following features: ability to use an intermediate pulse intensity (e.g., P−<15 MPa; P+<60 MPa) to mechanically deform the tissue without cavitation and without tissue ablation; and ability to use an intermediate pulse intensity (e.g., P−<15 MPa; P+<60 MPa) to exert oscillatory forces and shear stress on the tissue; ability to use an intermediate pulse pressure (e.g., P−<15 MPa; P+<60 MPa) to mechanically deform the tissue without cavitation and without tissue ablation; and ability to use an intermediate pulse pressure (e.g., P−<15 MPa; P+<60 MPa) to exert oscillatory forces and shear stress on the tissue.

Other various embodiments of the present disclosure can include aspects of drug delivery and drug activation using pulsed non-thermal, non-cavitational ultrasound therapy. For example, methods of the present disclosure can be used to temporally disrupt membranes to permit therapeutic agents to cross one or more membranes and reach their targets. Other embodiments can include using the histoplasty process to activate ultrasonically sensitive compounds that either become active therapeutic compounds themselves, or release active therapeutic compounds at the therapy site.

Using the histoplasty process to break drug resistant barriers (cell membranes, skin, cardio-vascular and blood-brain barriers, intestine, uterine lining, bladder lining, disease related granulomas, etc.), the feedback and monitoring processes of the present disclosure allow control of the tissue disruption process, enabling spatial disruption of tissues with minimal or no permanent tissue damage. These methods are possible due to the feedback and monitoring methods described herein. Consequently, the methods of the present disclosure can be used to deliver or enhance delivery or associated delivery of therapeutic agents, including pharmaceuticals (drugs), nano-particles, nucleic acids including DNA, RNA, and recombinant constructs, or other non-drug particles of molecules. The drug delivery process can use the feedback processes described herein in order to monitor the progress of the histoplasty process in real time or in stages.

Other various embodiments of the present disclosure can include aspects of altering the structure and organization of the ECM of the CNS using pulsed non-thermal, non-cavitational ultrasound therapy. For example, methods of the present disclosure can be used to temporally disrupt the PNN density in the brain.

Other various embodiments of the present disclosure can include aspects of various tissue disruption applications, such as tumor disruption, cancer-associated fibroblasts (CAFs) disruption, collagen fiber disruption in, e.g., breast tissue, liver tissue, pancreas tissue, brain tissue, and the methods disclosed herein can be used in applications where tissue is deformed (i.e., remodeled, rearranged, or disrupted) in cancer treatments.

Focused Ultrasound for Modulating Perineuronal Net (PNN) Density

Figure 6:
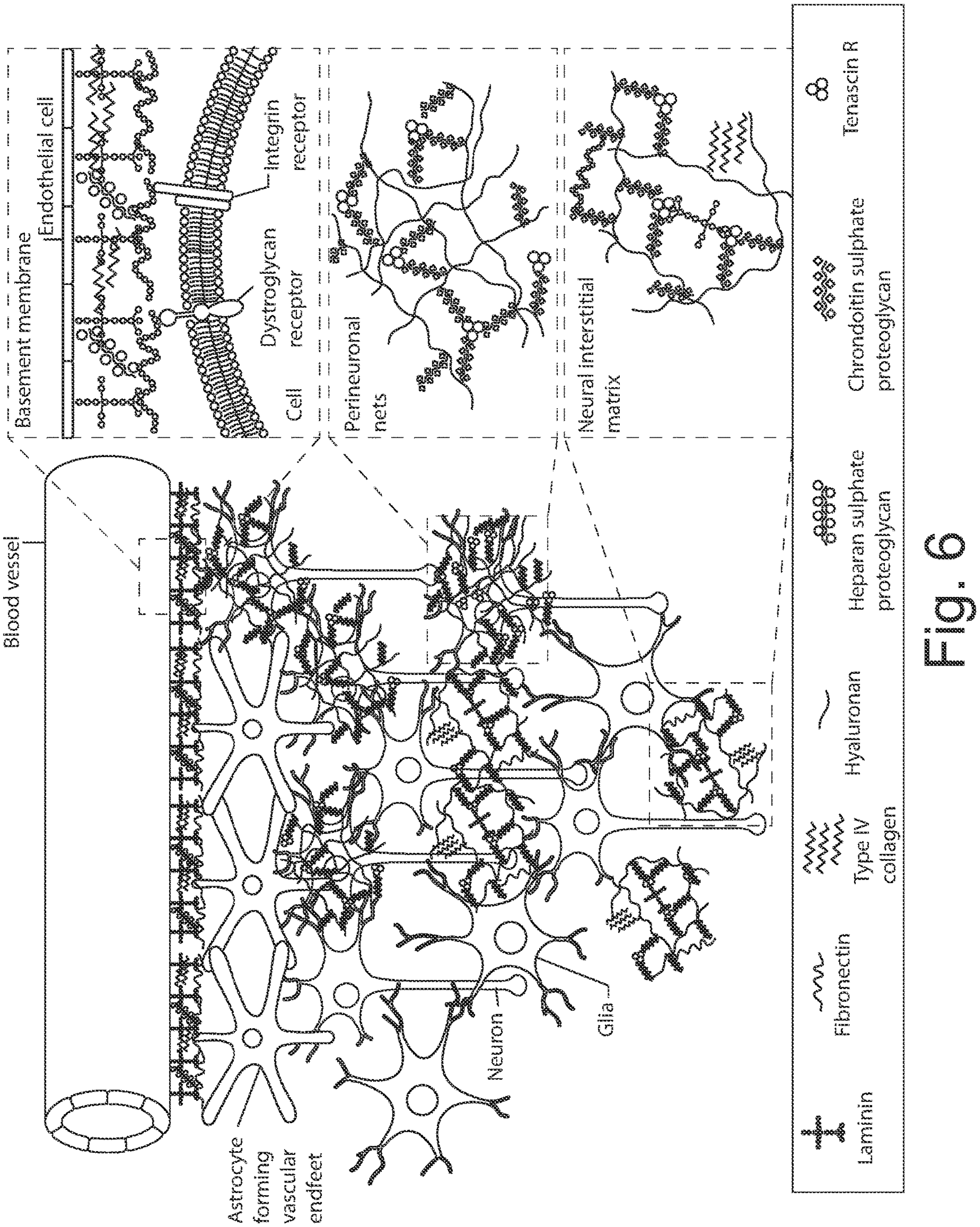
FIG. 6 is a schematic diagram of the CNS extracellular matrix of the brain with an enlarged view of the PNNs constituting a neural interstitial matrix.
Figure 7:
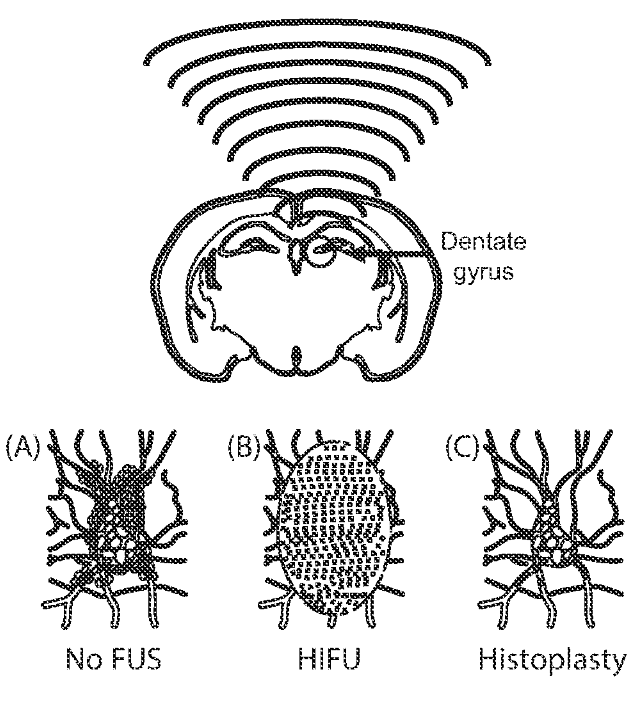
FIG. 7 is a schematic diagram of the PNNs (dentate gyrus) serving as a biological target for transcranial focused ultrasound (tFUS) and further showing (A) PNNs surrounding synaptic boutons on neuronal soma and proximal dendrites and consisting of chondroitin sulfate proteoglycans (CSPGs), (B) conventional tFUS approaches like high intensity focused ultrasound (HIFU) forming large tissue ablation cavities in the focal zone of the insonated ultrasound beam, (C) use of a non-ablative targeted tFUS technique specifically designed to decrease PNN density in the brain while leaving normal neural and neuroglial structures intact (no PNNs)

Referring to FIGS. 6 and 7, neurologic and neuropsychiatric disorders are a leading cause of disability and death worldwide. Underpinning the pathophysiology of these disorders are alterations to PNNs, which are a specialized component of the ECM of the CNS. In the CNS, the ECM comprises approximately 20% of the brain's volume and is principally composed of PNNs. PNNs are unique lattice-like structures which wrap around neurons and form tight interdigitations with synaptic contacts on neuronal bodies and proximal dendrites.

Scientific and clinical interest in PNNs has arisen from studies demonstrating the wide range of diseases and disorders PNNs contribute to, including effects on spinal cord injury, learning and memory, and psychiatric disorders such as schizophrenia, bipolar disorder, and addiction. With PNNs serving multiple critical homeostatic functions in the developing and adult brain and in the etiopathogenesis of multiple disparate neurologic disorders, the central role of PNNs in neurologic health and disease highlights PNNs as an attractive therapeutic target for the treatment of neurologic and neuropsychiatric illness. However, current studies for altering PNN density are restricted to preclinical models requiring the stereotactic injection of the enzyme chondroitinase-ABC (chABC) and the development of FUS techniques for neurologic illness have been hampered by the aberration and distortion of sound waves as they pass through the skull.

Referring specifically to FIG. 7, the present invention targets and treats intracranial neuropathology by using non-invasive transcranial focused ultrasound (tFUS) to physically alter the ECM of the CNS, specifically PNN density. Utilizing the compressive and shear forces produced by FUS during insonation, these forces can be tailored to mechanically shape and alter the ECM, thereby altering the biophysical organization and makeup of the ECM of the CNS.

CNS applications of FUS have conventionally used the thermo-ablative properties of techniques like HIFU to successfully treat essential tremor, neuropathic pain, and Parkinson's disease. Non-ablative FUS applications have also been developed and include work combining FUS with microbubbles (MBs) to open the BBB. However, prior studies have found that FUS with MBs (FUS+MB) for BBB opening results in an immediate damage-associated molecular pattern (DAMP) inflammatory response. When coupled with the complex challenges of MB dosing and timing and the anatomic challenges and long procedure times in HIFU, these factors together temper the potential to use current FUS and FUS+MB approaches to modulate the density or integrity of other structures in the CNS like PNNs in the ECM.

The present invention utilizes FUS to target mesoscopic structures within the CNS, e.g., PNNs in the ECM, for clinical translational applications. For example, the mechanical forces of FUS techniques can be employed without MBs and the known associated DAMP inflammatory response. The bioeffects of the present invention span the gamut of microscopic bioeffects with mechanical deformation of the neuronal membrane and activation of mechanosensitive ion channels to gross tissue changes with the generation of bulk tissue ablation cavities with histotripsy highlighting the substantial range of bioeffects possible with tFUS and this technology. These bioeffects traverse vast scales both in the size of targets affected (molecular to bulk tissue) and the ultrasonic energies used.

The following non-limiting examples illustrate the compositions, methods, and applications of the present teachings.

EXAMPLES

Example 1: Transcranial FUS (tFUS) without Microbubbles Targeting PNNs

Techniques like low intensity focused ultrasound (LIFU), high intensity focused ultrasound (HIFU), and histotripsy have all demonstrated histologic evidence of successful lesion targeting, sharply demarcated treatment margins, and the absence of histological injury in the near field beam path. This is made possible, in large part, to treatment plans that avoid near field thermal heating effects, which inform and guide the timing and dosing of acoustic energies used.

In the prior art methods, to avoid iatrogenic thermal injuries, tFUS has been paired with MBs. Following ultrasound excitation, MBs can collapse during the positive pressure cycle in a phenomenon known as inertial cavitation. The mechanical energy resulting from MB cavitation reduces the acoustic intensity needed to generate the desired mechanical forces, further reducing the risk of thermal injury.

The present invention provides that tFUS can produce mechanical forces matched to the physical scale of PNNs without MBs. FUS (without MBs) can produce targeted and scale-appropriate mechanical forces and bioeffects at the physical scale of PNNs. Previous published work has demonstrated that FUS can induce targeted neuronal activity as a result of mechanical forces generated from the ultrasound beam alone, and in the emerging field of sonogenetics, FUS can stimulate neuronal activity in mice expressing the human transgenic mechanosensitive ion channel, hsTRPA1. FUS has been demonstrated to produce physiologic effects arising from FUS activation of molecular targets, indicating that analogous efforts targeting of the structure of PNNs in the ECM of the CNS is technically feasible and accessible with tFUS.

Figure 8:
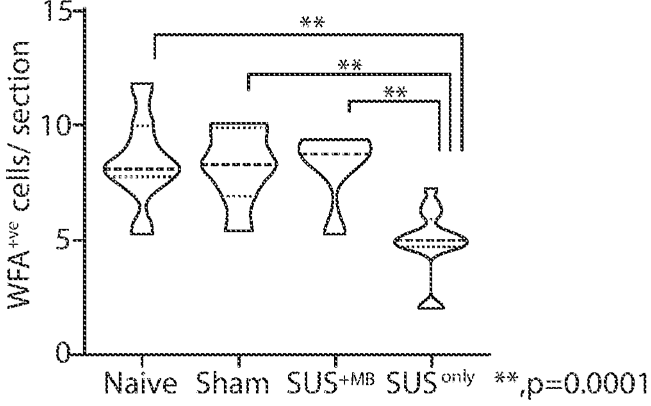
FIG. 8 is a chart showing a significant decrease in $WFA^{+ve}$ cells (PNN-positive cells) in the dentate gyrus of animals treated with $SUS^{only}$ (one-way ANOVA [F(3,27)=9.963, p=0.0001], Bonferroni post hoc analysis)

The present invention recognizes that tFUS can be used to disrupt the ECM and decrease PNN density. Referring to FIG. 8, there is experimental evidence demonstrating that mechanical forces from FUS can produce highly specific molecular bioeffects in the brain on the scale of PNNs. In a study examining the effect of FUS in the aged, senescent mouse brain, it was discovered that treatment with FUS without MBs was able to restore long-term potentiation (LTP) and restore spatial learning deficits of the aged mice. This functional improvement was associated with increased neurogenesis, synaptic signaling, and a significant decrease in PNN density.

PNNs typically assemble around parvalbumin (PV)-expressing interneurons and stabilize synaptic connections. In doing so, PNNs limit synaptic plasticity, which has been shown in numerous neural circuits including the developing visual system, fear memories, and CA2 (Carbonic Anhydrase 2) plasticity in a murine model of Rett syndrome. Enzymatic degradation of PNNs restored synaptic plasticity, much in the same way tFUS was able to decrease PNN density and contributed to functional recovery in the aged, senescent mouse brain. A SWATH-MS analysis was performed and scanning US only ($SUS^{only}$) FUS animals showed no significant fold changes in proteins associated with (neuro)inflammation, suggesting both the safety and efficacy of tFUS-mediated PNN degradation.

Therefore, instead of relying on MBs to exert structural bioeffects, the present invention leverages the well-described mechanical effects of ultrasonic pressure fields on PNNs to achieve a wide and tunable range of desired bioeffects on the CNS.

Example 2: Optimize Transcranial Histoplasty Parameters for Degradation of PNNs in the Murine Brain Prior art FUS parameters (i.e., high ultrasound frequency, large duty cycle) preclude direct clinical translation and motivate the rational design of clinically translatable FUS parameters targeting PNNs. The present invention provides a rational design of a clinically translatable FUS protocol for targeted alterations to PNNs in the brain.

The present invention sonicates cortical (i.e., somatosensory cortex) and subcortical (i.e., dentate gyrus) targets in the murine brain across a wide and clinically translatable parameter space (i.e., transducer frequency, pulse duration, peak negative pressure) to determine an ideal FUS protocol for depletion of PNNs in the murine brain.

Experimental Design

Animals: 6-8-week-old male and female inbred WT mice (C57BL/6J, Jackson Laboratory, USA) are randomly assigned to an experimental treatment group (see FIG. 10) with 6 replicates per sex, per experimental group (n=54 per sex; ntotal=108 animals). Sample sizes for power calculations are alpha=0.95 and a desired power value of 0.80. Sex is included as a biological variable as sex-specific differences in PNN density are unknown and sex-specific responses to a new FUS insonation protocol are also unknown. tFUS treatment are only performed in the left hemisphere; the right hemisphere undergoes a sham (control) treatment whereby the anesthetized animal is head restrained and placed under the transducer head but without ultrasound treatment.

FUS treatment: Under continuous isoflurane anesthesia, mice undergo in vivo tFUS treatment using a custom-built small animal system designed to target the mouse hippocampus.

An example of a small animal system designed for tFUS studies is shown in FIG. 9A. An exemplary apparatus 200 for performing pulsed non-thermal, non-cavitational ultrasound therapy constructed in accordance with the teachings of the present disclosure is shown. The apparatus can comprise a therapy transducer 202 and an imaging probe 204 coupled to a 3-axis positioning system 206. The therapy transducer 202 and imaging probe 204 are submerged in a circulating water tank 205 and focus ultrasound onto the mouse hippocampus 208 of a mouse positioned on the subject stage 207. Computer control and data collection 212 is coupled to an electronic driving system 214 that is further coupled to a power supply 216 which may power the electronic driving system 214, computer control and data collection 212 and the therapy transducer 202.

Referring to FIG. 9B, a modular 1-MHz transducer 202 is designed to precisely allow FUS to be delivered to the mouse hippocampus 208. The 1-MHz transducer 202 is constructed from piezoceramics with matching layers and injection-molded acoustic lenses to maximize robustness and ability to clean. The geometric characteristics of the acoustic lens are based on the desired anatomic targets in the murine brain. The 1-MHz transducer 202 is designed with a max targeting depth of 5-mm and focal dimensions of approximately 1-mm, 1-mm, and 3-mm in the transverse, axial and elevational directions, respectively.

Figures 10, 11:
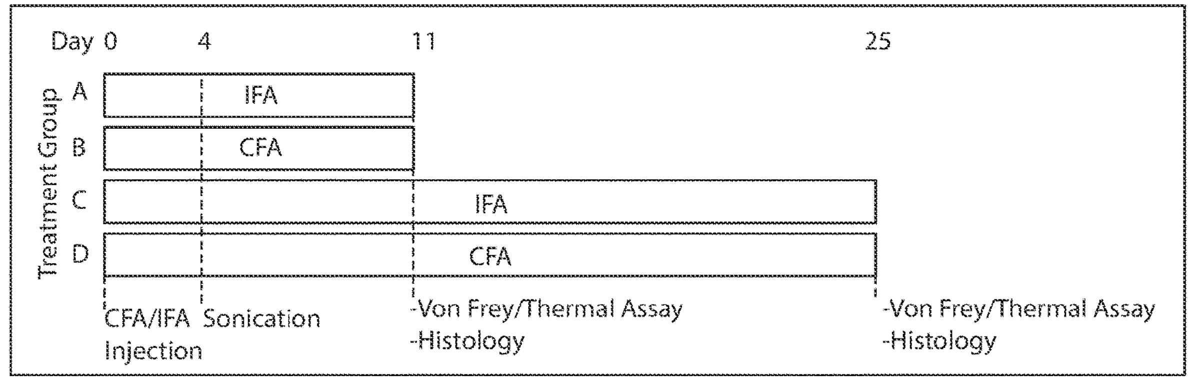
FIG. 10 is a table showing histoplasty parameters to be tested in Examples 2 and 3 (Low, intermediate, and high peak negative pressures are tested. Initial duty cycle parameters are chosen to negate any thermal effects. 6 replicates are performed for each combination of peak negative pressure, duty cycle, and duration. For all conditions, fundamental frequency=1 Mhz, PRF=500 Hz. ([a])=FUS parameters that induced PNN loss as shown in FIG. 7 and is included here as a positive control)
FIG. 11 is an experimental design of Example 4 where, following injection of incomplete Freund's adjuvant (IFA) or complete Freund's adjuvant (CFA) in the right hindpaw of the mice, the left somatosensory cortex (SSC) are sonicated on day 4 and Von Frey filament testing, thermal testing, and quantitative histology (PNN density) is performed on day 11 or day 25.

The k-Wave MATLAB toolbox is used to simulate the acoustic field and focal waveforms for the treatment parameters outlined in the table of FIG. 10. The element response is modeled with a KLM-based 1-D piezoelectric simulation. A custom high-voltage pulser is built to drive the transducer while being controlled by a field-programmable gate array (FPGA) board (Altera DEO-Nano Terasic Technology, Dover, DE, USA) programmed for FUS therapy pulsing and powered by a high-voltage DC power supply (GENH750 W, TDK-Lambda). The acoustic field generated by the transducer 202 is measured by fiber optic hydrophone (FOPH) or imaging probe 204 affixed to a computer-controlled 3-axis positioner 206. The system is calibrated at the focus by recording pressure waveforms as a function of the input voltage to the amplifier and position relative to the focus.

FUS treatments are performed on a warmed stereotaxic stage 207 coupled to a computer-guided positioning system 206 on a 3-D axis with 0.05-mm motor resolution to permit precise stereotactic targeting of the left somatosensory cortex (SSC) and the left dentate gyrus (DG) of the hippocampus using stereotactic coordinates; this is attached to the transducer 202 and controlled by a custom user interface operated through MATLAB (The MathWorks, Natick, MA, USA).

The acoustic parameters are chosen to span the full range of clinically relevant acoustic parameters capable of inducing PNN degradation, ranging from low pressure pulsing methods commonly used in LIFU applications to high pressure exposures approaching those used in histotripsy but remaining below the threshold for generating cavitation. Higher pressure treatments are specifically included here as they have the added advantage of employing lower duty cycles that can prevent undesired thermal effects. The SSC and DG are selected as sonication targets due to differences in the depth of target within the brain and as both possess different densities of PNNs. Importantly, the projected beam path to the SSC and DG are planned to be along two, non-overlapping different beam paths. Continuous cavitation and thermal monitoring is performed with an omnidirectional hydrophone (AS-1, Aquarian Scientific, Anacortes, WA) and a needle thermocouple (MT-23/5HT, needle microprobe, Physitemp Instruments, Clifton, NJ), respectively.

Brain tissue preparation, confocal microscopy, and image analysis: Brain samples are processed. One hour following sonication and sham FUS treatments, animals are perfused with ice-cold PBS. Brains are dissected and fixed in paraformaldehyde, floated in sucrose, and frozen in freezing media. 20 μm thick frozen sections are cut on a frozen cryostat. PNNs are stained with biotin-*Wisteria floribunda* agglutinin (WFA, 1:2500, Vector Labs, #B1355) primary antibody followed by streptavidin 555 (1:1000, Molecular Probes) and DAPI (1:5000, Sigma-Aldrich) counterstained. All sections are imaged using a Nikon Alit confocal microscope with confocal images to be acquired with a 63× objective (oil immersion). Fluorescence intensity is quantified using FIJI.

To analyze WFA fluorescence intensity, all sections are processed and imaged concurrently. Exposure settings on the epifluorescence microscope are maintained across all acquired images. To quantify fluorescence intensity in the sonicated and contralateral (non-treated) DG and SSC, a fixed contour is positioned over each region and an 'integrated density' is measured. For each set of parameters (peak negative pressure, duty cycle, and exposure duration), a 2-way ANOVA (sex, treatment) is used to compare WFA fluorescence intensity between each sonicated regions (DG; SSC) and the contralateral (sham) regions. Researchers are blinded to animal treatment groups and tissue laterality.

Statistical modeling and data analysis: In addition to planned ANOVA analyses, to determine optimal sonication parameters, WFA fluorescence intensity (WFA+, PNN density) are regressed against the FUS experimental parameters (peak negative pressure, duty cycle, and exposure duration) with biological sex included as a categorial covariate. As groups of animals undergo FUS treatment in cohorts, 'cohort' is included as a second categorical covariate. Interaction effects are not modeled due to our experimental design. If any relationship between WFA+ and a variable are seen to be non-linear (as evidenced by a scatterplot), higher order polynomial effects are modeled; a fit to a non-linear regression model may also be pursued; however, this is less favored due to the absence of a specified function. The construction of a multiple regression model allow for the testing and identification of important variables to the overall regression model as evidenced by the standard error of each coefficient (e.g., high standard error, low overall contribution to effect), which can inform iterative parameter optimization in planned subsequent rounds of testing. Following regression, the sign of the calculated coefficients inform the direction to which each parameter can be further optimized (positive sign, smallest possible value; negative sign, largest possible value as a minimum in WFA+intensity is the desired outcome).

Results

A combination of tFUS parameters (peak negative pressure, duty cycle, and exposure duration) able to effectively decrease PNN density in the murine brain is determined for two different regions of interest (SSC; DG). PNN degradation is observed at the lowest set of parameters tested and the degree and extent to which PNN degradation is observed is expected to increase with tFUS treatments delivered at higher pressures and longer exposure times, with complete degradation of PNNs achieved when exposed to the high amplitude exposures. These high-pressure exposures are chosen to induce significantly larger mechanical effects on the tissue without inducing any significant thermal effects (duty cycle <1%). The combination of analytic approaches employed (2-way ANOVA; statistical analysis with multiple regression) provide both a granular and inclusive understanding of the effect of different FUS parameters on PNN density.

It is possible cavitation may occur. To ensure cavitation is not a contributing bioeffect, passive cavitation monitoring is performed in all experiments. If cavitation is observed, numerous experimental parameters can be modified including reducing the peak negative pressure and duty cycle from the initial parameters proposed in the table of FIG. 10. Thermal effects may also be present. If thermal effects are observed, a very low duty cycle may be used for the high-pressure treatment groups. These carefully selected parameters can be further modified if an increase in temperature is observed. The presence of skull ultrasound aberration and attenuation may be observed. To address this, parameters may be chosen which can target the brain transcranially in small animal models. Acoustic beam modeling knowledge can be used to address targeting concerns.

Example 3: Determine the Biological Effects and Safety Profile of Histoplasty Histological studies of brain tissue following LIFU, HIFU, and histotripsy have demonstrated the absence of histological injury around the focal zone as well as in the near field beam path. However, a significant gap in knowledge is the absence of a complete understanding of the molecular and cellular effects of tFUS. Recent work demonstrates BBB opening with FUS+MB produces a sterile inflammatory response (SIR) with early neuronal and astrocytic injury, astrocyte and microglial activation, and increased expression of CAM.

As other FUS techniques without MBs can produce desired bioeffects without concomitant neuronal injury the present invention provides that (i) SIR is induced by MB bioeffects and (ii) the proposed histoplasty technique does not produce a SIR as no MBs are used. The present invention performs quantitative immunofluorescence and quantitative real-time PCR following tFUS histoplasty of the left dentate gyrus to determine the molecular and cellular response to histoplasty treatment.

Experimental Design

Animals: 6-8-week-old male and female inbred WT mice (C57BL/6J, Jackson Laboratory, USA) are randomly assigned to an experimental group (see FIG. 10) to undergo transcranial focused ultrasound. 8 replicates per sex, per experimental group (n=4 for RT-PCR; n=4 for quantitative histology) are planned for each experimental group (n=72 per sex; ntotal=144 animals). Sample sizes for power calculations are alpha=0.95 and a desired power value of 0.80. As in Example 2, sex is included as a biological variable as sex-specific differences in the molecular and cellular response to a newly developed FUS insonation protocol are unknown. tFUS treatment is only performed in the left DG; the right DG undergoes a sham (control) treatment whereby the anesthetized animal is head restrained and placed under the transducer head but without ultrasound treatment. As the FUS parameters tested in Example 3 are identical to those used in Example 2 (see FIG. 10), this will facilitate the comparison of PNN density findings to other biological data analyzed in this Example 3.

FUS treatment: Using identical FUS procedures outlined in Example 2, mice undergo in vivo tFUS treatment using the previously described custom eight-element, small animal FUS transducer. tFUS treatments (FIG. 10) are performed on a warmed stereotactic stage coupled to a computer-guided positioning system on a 3-D axis with 0.05-mm motor resolution to permit stereotactic targeting of the left dentate gyrus of the hippocampus.

RNA isolation and quantitative real-time PCR: 6 hours following sonication, brains are dissected en bloc and the left (sonicated) and right (sham/control) dentate gyrus are isolated and extracted into RNAlater (Ambion) and stored at −20C. cDNA synthesis is performed (RT2 First strand Kit, Qiagen) followed by quantitative RT-PCR with RT2 SYBR Green qPCR Master Mix (Qiagen). cDNA samples from each group are screened with RT2 Profiler PCR Array Mouse NFκB Signaling Pathway (Qiagen). Array expression data is analyzed using the SABiosciences PCR Array Data Analysis platform. The 6-hour timepoint is chosen based on prior work demonstrating maximal mRNA fold-changes seen following insonation with FUS+MB.

Histological staining: 6 hours post sonication, all animals are perfused with ice-cold PBS. Brains are dissected and fixed in paraformaldehyde, floated in sucrose, and embedded in optimum cutting temperature tissue-mounting medium and sliced into 20 μm thick frozen sections on a frozen cryostat. Immunostaining is performed for ICAM, GFAP, and Iba1. Isotype antibodies are used as a negative control. As in Example 2, brain samples are imaged using a Nikon Alit confocal microscope with confocal images to be acquired with a 63× objective (oil immersion). Fluorescence intensity is quantified using FIJI from three sections from each animal. To analyze ICAM, GFAP, and Iba1 fluorescence intensity, all sections are processed and imaged concurrently and exposure settings on the epifluorescence microscope are maintained across all acquired images. To quantify fluorescence intensity in the sonicated and contralateral (non-treated) DG, a fixed contour is positioned over each region and an 'integrated density' is measured.

Statistical Analysis: A 2-way ANOVA (sex, treatment) is used to compare ICAM, GFAP, and Iba1 fluorescence intensity between the sonicated and the contralateral (sham) DG. Researchers are blinded to animal treatment parameters and laterality during IF quantitation.

Data analysis: To determine the potential inflammatory effect of insonation with the histoplasty protocol, within each experimental group, a heat map is derived from the qRT-PCR array data, which includes 84 genes related to the NEκB pathway with fold changes compared to the contralateral sham treated brain. A Venn diagram is constructed to determine overlapping changes in mRNA expression between experimental groups (both within and intersex). Functional genetic analyses such as GO and KEGG is performed to gain insight into the functional significance of differentially expressed genes, if any.

Results

Minimal, if any, changes associated with a sterile inflammatory response and neuroinflammation are expected. No significant changes are expected in mRNA transcript number in the sonicated left DG compared to the right as they pertain to NEκB signaling pathway. Little to no significant astrocyte or microglial activation or significant ICAM staining is expected that would suggest neuroinflammation. Therefore, the present invention provides an absence of cytotoxic and iatrogenic inflammatory effects from the sonication protocol, and an absence of physiological changes in tFUS protocols without MBs.

It is possible that the sonication protocols used demonstrate evidence of sterile inflammation. If this is observed, numerous experimental (sonication) parameters can be modified including peak negative pressure, duty cycle, and the exposure duration beyond the initial parameters in the table of FIG. 10.

Example 4: Determine if PNN Degradation by Histoplasty can Produce Analgesia in a Murine Model of Chronic Pain Over 1 in 5 U.S. adults (nearly 50 million) report chronic pain. Chronic, untreated pain affects sleep, cardiovascular health, and mental health and is associated with significant economic costs. To understand the biological mechanisms underlying chronic pain, recent work found increased deposition of PNNs in the corresponding somatosensory cortex (SCC) of a murine model of chronic hindlimb pain. Remarkably, enzymatic degradation of PNNs in the affected SSC reduced both mechanical and thermal pain, suggesting a causal link between increased PNN density and the development of nociceptive pain in the SSC.

The present invention provides an accessible, rapid, and translational model of chronic inflammatory pain. The present invention provides that tFUS-mediated degradation of PNNs in the affected SSC can reduce PNN density and associated mechanical and thermal pain. Differences in pain thresholds (Von Frey assay; thermal assay) before and after histoplasty sonication of the affected SSC are assessed.

Experimental Design

Figures 12, 13:
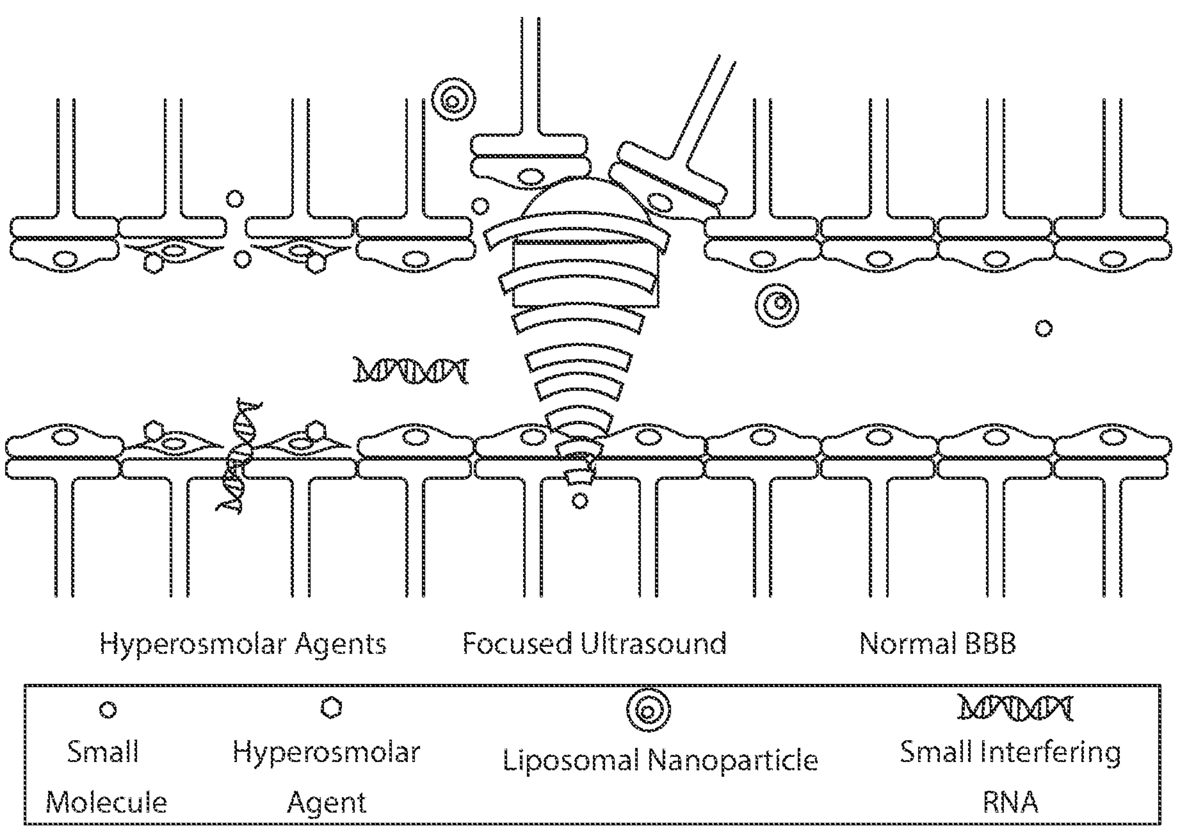
FIG. 12 is a table showing low, intermediate, and high peak negative pressure parameters to be tested in Example 4 (Initial parameters are chosen to negate any thermal effects. 6 replicates are performed for each combination of peak negative pressure, duty cycle, and exposure duration per sex, per treatment group. For all conditions, fundamental frequency=1 Mhz, PRF=500 Hz. (a)=FUS parameters that induced PNN loss as shown in FIG. 7 and is included here as a positive control)
FIG. 13 is a schematic diagram of the blood-brain barrier modulation mechanism of FUS and hyperosmolar agents showing hyperosmolar agents disrupting the BBB via dehydration of endothelial cells, causing contraction and disruption of temporoparietal junctions, thus allowing indiscriminate paracellular transit of solutes from the abluminal vascular compartment to the brain and the FUS insonation without microbubbles disrupting the microvascular endothelium.

Animals: 6-8-week-old male and female inbred WT mice (C57BL/6J, Jackson Laboratory, USA) are randomly assigned to one of four experimental groups (n=48 per experimental group; n=24 per biological sex; $n_{total}$=192) (FIG. 12). The overall experimental design is outlined in FIG. 11; experimental paradigms for a well-characterized model of induction of chronic inflammatory pain and subsequent pain testing follow below.

Within each experimental group, animals are randomly assigned to a treatment group (A-D, n=6 per treatment group) (see FIG. 11). All animals undergo tFUS treatment to the left S1 SSC on day 4 and pain threshold testing (Von Frey filament and thermal assays) on day 11 (1 week post FUS; acute treatment related changes) or day 25 (3 weeks post FUS; chronic treatment related changes). Sex is included as a biological variable as sex-specific differences and potential responses to histoplasty sonication and PNN depletion in a model of chronic inflammation are unknown. FUS treatment is only performed in the left SSC; the right SSC undergoes a sham (control) treatment whereby the anesthetized animal is head restrained and placed under the transducer head but without ultrasound treatment. The FUS parameters tested in this Example 4 are a subset of previously tested FUS parameters from Examples 2 and 3 across low, intermediate, and high negative pressures, which also includes the tFUS condition already known to show PNN degradation as shown in FIG. 8.

Induction of chronic inflammatory pain: Tissue inflammation is induced by subcutaneous injection of complete Freund's adjuvant (CFA) (20 μL, 1 mg/mL) in the plantar surface of the right hindpaw (Treatment Groups B/D, FIG. 11). Control mice are injected with incomplete Freund's adjuvant (IFA), in the plantar surface of the right hindpaw (Treatment Groups A/C, FIG. 11).

Pain testing (mechanical and thermal): The Von Frey hair assay (mechanical pain testing) is used to measure mechanical pain thresholds using the protocols previously described. Following habituation to the testing chamber, the plantar surface of each hindpaw is stimulated 5× with a weighted Von Frey hair monofilament. An observer blinded to the experimental/treatment groups monitors and records instances of hindpaw withdrawal to stimulation. Hindpaw stimulation is repeated through progressive series of filament weights (0.04-2.0 g). Left and right hindpaw responses are averaged within each animal to provide a combined threshold for each test day. A warmed stage is used to measure thermal pain thresholds. Mice are placed on a 500° C. heated surface and the time to the first sign of nociception (licking of hindpaw, jumping) is recorded and the animal immediately removed. Mice are tested on days 11 (acute response to treatment) and 25 (chronic/durable response to treatment).

FUS treatment: Using identical FUS procedures outlined in Examples 2 and 3, mice undergo in vivo tFUS treatment using the described custom eight-element, small animal FUS transducer. Prescribed FUS treatments (FIG. 12) is performed on a warmed stereotactic stage coupled to a computer-guided positioning system on a 3-D axis with 0.05-mm motor resolution to permit stereotactic targeting of the left S1 SSC.

Histological staining: On days 11 and 25, following testing, animals are perfused with ice-cold PBS. Brains are then dissected and fixed in paraformaldehyde, floated in sucrose, and embedded in optimum cutting temperature tissue-mounting medium and sliced into 20 μm thick frozen sections on a frozen cryostat. As described in Example 2, PNNs are stained with biotin-*Wisteria floribunda* agglutinin and imaged using a Nikon Alit confocal microscope. Fluorescence intensity is quantified using FIJI with fluorescence intensity in the sonicated and contralateral SSC. Within each experimental group, a three-factor ANOVA (sex, treatment, acute/chronic) is used to compare WFA fluorescence intensity left SSC (treated) and right SSC (control). Researchers are blinded to animal treatment parameters and tissue sample laterality.

Statistical modeling and data analysis: WFA fluorescence intensity is regressed against FUS experimental parameters used including transducer frequency and exposure duration, with biological sex, treatment group, and chronicity included as a categorial covariates. Groups of animals undergo FUS treatment in cohorts, 'cohort' is included as an additional categorical covariate. Interaction effects are not modeled due to the experimental design. If any relationship between WFA+ and a variable are seen to be non-linear (as evidenced by a scatterplot), higher order polynomial effects are modeled; a fit to a non-linear regression model may also be pursued but is less favored due to the absence of a specified function.

Results

Histoplasty treatment of the left S1 SSC is expected to reduce mechanical and thermal pain, consistent with prior reports suggesting a causal link between increased PNN density and the development of nociceptive pain in SSC. This would be commensurate with decreased PNN density from FUS treatment in the affected SSC. The durability of histoplasty treatment is determined by examining acute and chronic changes in PNN density in the SSC. The present invention demonstrates a quantifiable improvement in pain tolerance following histoplasty treatment, suggesting a causal link between ultrasound insonation and decreased PNN density that helps support the clinical translational potential of histoplasty treatment. It is possible that the sonication protocols used in this Example 4 do not decrease PNN density in the SSC as predicted. If this potential floor effect is observed, as before, sonication parameters are modified including peak negative pressure, duty cycle, and the exposure duration beyond the initial parameters proposed in the table of FIG. 12. It is also possible that other bioeffects from FUS may drive behavioral changes in the animals such as small thermal effects or other functional changes (e.g., neuronal stimulation) and the mechanisms and effects of these observed changes explored.

Focused Ultrasound for Opening the Blood-Brain Barrier (BBB)

Referring to FIG. 13, Alzheimer's disease (AD) is a complex, multifactorial neurodegenerative disorder that affects an estimated 5.8 million Americans and is the 6th leading cause of death in the United States. Novel anti-amyloid (Aβ) monoclonal antibodies such as donanemab, lecanemab, and aducanumab represent an exciting new class of drugs directed at the underlying pathophysiology of AD. However, anti-Aβ immunotherapy approaches, like many other therapeutics designed to treat neurodegenerative, neuro-oncologic, and neuroinflammatory illness, are significantly limited by their ability to efficiently cross the BBB. This limitation highlights the acute need for innovative drug-delivery strategies that can specifically and transiently open the BBB and permit the transit of therapeutics from the intravascular compartment to the brain.

The BBB consists of specialized endothelial cells that are connected through various tight junction proteins (TJP), astrocyte endplates, and a basement membrane and highly restricts the transport of biomolecules from the intravascular space to the brain. Although the BBB functions as a critical physiological, structural, and functional barrier, the stringent barrier properties of the BBB also impede the effective delivery of therapeutic compounds to the brain. With the fast emerging development of new drugs targeting the CNS including those for AD, amyotrophic lateral sclerosis, and Parkinson's disease, there is an urgent need for a safe and effective BBB modulator that can enhance the therapeutic potential of these and other forthcoming pharmacologic treatments targeting the CNS.

Despite the growing need to efficiently deliver therapeutics across the BBB, there are several critical gaps in knowledge that currently limit our ability to do so both safely and effectively. Various techniques and approaches have been explored to modulate the BBB including small molecules (mannitol), peptide and peptidomimetics, proteins (monoclonal antibodies), and FUS. FUS has garnered intense interest due to the non-invasive and targeted nature of the technique, but consistent FUS parameters for BBB disruption without damage to the surrounding brain parenchyma have not been reported. To address this shortcoming, newer FUS approaches to BBB disruption have introduced the use of microbubbles (MBs), where MBs driven by the cycles of compression and rarefaction of ultrasound exert stresses on surround blood vessel walls to temporarily open the BBB. Although preclinical and clinical studies have reported the safety and efficacy of the FUS+MB approach for BBB disruption, wide-ranging non-standardized protocol factors like pulsing scheme and MB size, dose, and shell composition highlight the ongoing clinical translational challenges of the FUS+MB technique.

The safe clinical translation of FUS techniques for BBB disruption entails a comprehensive understanding of the potential biological effects that FUS treatment might provoke. Although early BBB disruption studies examining the effect of FUS and FUS+MB on the brain found no significant evidence of post-procedural hemorrhage or ischemia, recent work using more sensitive and quantitative biomolecular techniques have identified notable side effects including neuronal suppression, astroglial scarring, cellular apoptosis, and sterile inflammation. The extensive biological effects of FUS+MB approaches to BBB disruption may be related in part to the coupling of FUS with MBs. Following insonation, MBs undergo cavitation and generate acoustic pressure waves (e.g., shockwaves) into the surrounding parenchyma that are difficult to control and activate microglia, astrocytes, and neurons beyond the vasculature. These side effects again underscore the technical difficulties associated with the use of MBs in targeted BBB disruption with FUS and the translational challenges that remain to be addressed. Overall, the ongoing challenges of FUS (and other molecular and non-invasive techniques) for BBB disruption underscore the compelling rationale for continued investigation and development of novel approaches and technologies that can safely and effectively open the BBB for delivery of therapeutics to the brain.

In contrast to modern FUS protocols relying on thermal (HIFU) or MB cavitation (FUS+MB, histotripsy) approaches to BBB disruption, histoplasty instead leverages the mechanical effects of high-intensity pressure fields generated by short-duration (<20 μs), high-amplitude pulsed US protocols to alter the local tissue microenvironment without cavitation and without tissue ablation. An advantage of histoplasty is the absence of MBs and MB cavitation, which suggests that many of the problematic biologic effects associated with MBs will be absent in histoplasty. Further, as histoplasty uses analogous pulsed ultrasound protocols to histotripsy, histoplasty enjoys many of the same exceptional performance characteristics including the production of precise and accurate lesions with sharp boundaries between treated and untreated tissue. The narrow width of the histoplasty ultrasound pulse also highly restricts the degree to which skull aberrations can induce and distort the ultrasound focus and the short pulse duration also allows histoplasty to be delivered rapidly while maintaining low duty cycles to avoid complications of tissue heating that are often encountered in other FUS technologies such as HIFU.

The following non-limiting examples illustrate the compositions, methods, and applications of the present teachings.

Examples

Example 5: Investigate Transcranial Histoplasty Parameters for Optimal Blood-Brain Barrier (BBB) Disruption FUS in combination with intravenously injected MBs can transiently open the BBB. However, FUS+MB opening of the BBB is limited by significant side effects such as microhemorrhage, sterile inflammation, and skull heating and substantial variances in microbubble dosing, size distribution, and shell composition that limit reproducibility and the clinical translation of FUS+MB approaches for BBB opening.

Experimental design: In 10-12 week old male and female inbred C57BL/6J mice, determine optimal histoplasty sonication parameters for transient BBB opening (peak negative pressure, pulse repetition frequency, and frequency) as measured by quantitative sodium fluorescein emission.

Example 6: Determine the Biological Effects of Histoplasty

FUS+MB opening of the BBB is known to induce numerous biological effects including sterile inflammation and altered protein expression; however, the biological effects of histoplasty-derived US protocols are unknown.

Experimental design: In experimental cohorts of age- and sex-matched control and 5XFAD AD mice undergoing histoplasty, determine the effect of histoplasty on (i) DTI and NODDI brain microstructure, (ii) global brain connectivity, (iii) and transcriptomic changes associated with opening of the BBB.

Results: The present invention is an innovative approach to opening the BBB and the introduction of a new non-ablative therapeutic regime of focused ultrasound is expected. Importantly, as the histoplasty technique is broadly tunable and generalizable, future development of the histoplasty technique will lead to a broad spectrum of clinical applications in the CNS and in other organ systems to create new and complementary approaches to noninvasively treat disease both in the CNS and throughout the whole body.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "an electronic computer" and "a processor" or "the microprocessor" and "the processor," can be understood to include one or more of these devices that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

References to "a processor" should be understood to include electronic computers, microprocessors, microcontrollers, FPGA devices, ASIC devices and similar programmable or program defined electronic circuits and collections of such devices that can communicate in a stand-alone and/or a distributed environment(s), and can thus be configured to communicate via wired or wireless communications with other processors. Furthermore, references to memory, unless otherwise specified, can include one or more processor-readable and accessible memory elements and/or components that can be internal to the processor or external to the processor and accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What I claim is:

1. A method for controlled mechanical degradation of an extracellular matrix of brain tissue of a patient, the brain tissue having a cavitation threshold at which cavitation occurs, the method comprising:

outputting a treatment ultrasound pulse sequence directed at a treatment portion of the extracellular matrix of the brain wherein the treatment ultrasound pulse sequence is at a pulse intensity that is less than the cavitation threshold and at least partially degrades the extracellular matrix of the brain tissue in the treatment portion;

concurrent with the outputting of the treatment ultrasound pulse sequence, monitoring an amount of mechanical degradation of the extracellular matrix of the brain tissue in the treatment portion;

concurrent with the outputting of the treatment ultrasound pulse sequence, adjusting the treatment ultrasound pulse sequence based on the monitoring of the amount of mechanical degradation of the extracellular matrix of the brain tissue; and wherein the ultrasound pulse sequence is comprised of pulses each having a length of less than or equal to 20 us and a duty cycle of less than or equal to 2%.

2. The method of claim 1 wherein a peak negative pressure of the treatment ultrasound pulse sequence is less than or equal to 20 MPa.

3. The method of claim 2 wherein a peak negative pressure of the treatment ultrasound pulse sequence is less than or equal to 15 MPa.

4. The method of claim 1 wherein a peak positive pressure of the treatment ultrasound pulse sequence is less than or equal to 60 MPa.

5. The method of claim 1 wherein a frequency of the treatment ultrasound pulse sequence is between 500 kHz and 1 MHz.

6. The method of claim 1 wherein a pulse repetition frequency (PRF) of the treatment ultrasound pulse sequence is between 250 Hz and 750 Hz.

7. The method of claim 1 wherein a duty cycle of the treatment ultrasound pulse sequence is less than or equal to 1%.

8. The method of claim 1 wherein pulse length of the treatment ultrasound pulse sequence is less than or equal to 15 usec.

9. The method of claim 1 wherein a number of pulses in the treatment ultrasound pulse sequence is 10 to 50 pulses.

10. The method of claim 1 wherein an exposure duration of the treatment ultrasound pulse sequence is less than 60 sec.

11. The method of claim 1 further including the steps of monitoring cavitation in the treatment portion; and adjusting the energy of the ultrasound pulse sequence based on the monitoring of cavitation in the treatment portion.

12. The method of claim 1 wherein the monitoring of the amount of degradation of the extracellular matrix of the brain tissue in the treatment region is performed using a monitoring ultrasound transducer.

* * * * *